(12) United States Patent
Karnezis (10) Patent No.: US 9,034,015 B2
(45) Date of Patent: May 19, 2015

(54) SURGICAL DEVICE FOR CORRECTION OF SPINAL DEFORMITIES

(76) Inventor: Ioannis Karnezis, Athens (GR)

( * ) Notice: Subject to any disclaimer, the term of this patent is extended or adjusted under 35 U.S.C. 154(b) by 135 days.

(21) Appl. No.: 13/133,405

(22) PCT Filed: Dec. 8, 2009

(86) PCT No.: PCT/GB2009/051672
§ 371 (c)(1),
(2), (4) Date: Jun. 8, 2011

(87) PCT Pub. No.: WO2010/067113
PCT Pub. Date: Jun. 17, 2010

(65) Prior Publication Data
US 2011/0251646 A1    Oct. 13, 2011

(30) Foreign Application Priority Data

Dec. 10, 2008 (GB) .................................. 0822507.0
Feb. 16, 2009 (GB) .................................. 0902416.7
Aug. 3, 2009 (GB) .................................. 0913457.8

(51) Int. Cl.
*A61B 17/70* (2006.01)
(52) U.S. Cl.
CPC .......... *A61B 17/7046* (2013.01); *A61B 17/7001* (2013.01); *A61B 17/7007* (2013.01); *A61B 17/7023* (2013.01); *A61B 17/7038* (2013.01)
(58) Field of Classification Search
CPC .................................................. A61B 17/7001
USPC .................. 606/256, 257, 261, 264, 265, 267
See application file for complete search history.

(56) References Cited

U.S. PATENT DOCUMENTS

| | | | |
|---|---|---|---|
| 4,987,892 A | 1/1991 | Krag et al. | |
| 5,387,212 A | 2/1995 | Yuan et al. | |
| 5,876,403 A | 3/1999 | Shitoto | |
| 5,951,555 A | 9/1999 | Rehak et al. | |
| 6,572,618 B1 | 6/2003 | Morrison | |
| 6,872,209 B2 | 3/2005 | Morrison | |
| 7,083,621 B2 * | 8/2006 | Shaolian et al. | 606/86 A |
| 7,811,311 B2 * | 10/2010 | Markworth et al. | 606/278 |
| 8,021,396 B2 * | 9/2011 | Winslow et al. | 606/264 |
| 8,163,024 B2 * | 4/2012 | Arnin | 623/17.15 |
| 8,216,281 B2 * | 7/2012 | Winslow et al. | 606/264 |
| 8,518,089 B2 * | 8/2013 | Gabele | 606/282 |
| 2003/0130661 A1 | 7/2003 | Osman | |

(Continued)

FOREIGN PATENT DOCUMENTS

| | | |
|---|---|---|
| EP | 0553424 A1 | 8/1993 |
| FR | 2891727 A1 | 10/2005 |

(Continued)

*Primary Examiner* — Ellen C Hammond
(74) *Attorney, Agent, or Firm* — Crose Law LLC; Bradley D. Crose (57) ABSTRACT

The present invention relates generally to a surgical device for the correction of deformities of the spinal column and finds particular, although not exclusive, utility in devices which are surgically implantable. Presently known implantable surgical devices are unable to provide for the progressive correction of spinal deformities assisted by active movements of the human body without fusion of the involved part of the spinal column. The present surgical device comprises a spinal column straightening means for permitting the relative rotation of two substantially adjacent vertebrae about a common axis substantially only in opposite rotational directions.

11 Claims, 9 Drawing Sheets

(56) References Cited

U.S. PATENT DOCUMENTS

| | | | |
|---|---|---|---|
| 2004/0010253 A1 | 1/2004 | Morrison | |
| 2005/0234451 A1* | 10/2005 | Markworth | 606/61 |
| 2005/0261770 A1 | 11/2005 | Kuiper et al. | |
| 2006/0149237 A1* | 7/2006 | Markworth et al. | 606/61 |
| 2007/0239159 A1 | 10/2007 | Altarac et al. | |
| 2007/0270808 A1* | 11/2007 | Drewry et al. | 606/61 |
| 2007/0276371 A1 | 11/2007 | Baynham et al. | |
| 2008/0306525 A1 | 12/2008 | Mitchell et al. | |
| 2009/0254127 A1* | 10/2009 | Pazanowski et al. | 606/286 |
| 2010/0004697 A1 | 1/2010 | Fortin et al. | |

FOREIGN PATENT DOCUMENTS

| | | |
|---|---|---|
| WO | 02/34150 | 5/2002 |
| WO | 2005/104970 | 11/2005 |
| WO | 2005104970 A1 | 11/2005 |
| WO | 2007117366 A2 | 10/2007 |
| WO | 2007121128 A1 | 10/2007 |
| WO | 2008121343 A1 | 10/2008 |

* cited by examiner

SURGICAL DEVICE FOR CORRECTION OF SPINAL DEFORMITIES

CROSS-REFERENCE TO RELATED APPLICATION

The present non-provisional patent application claims the benefit of priority of: foreign Patent Application No. GB0822507.0, which is entitled SURGICAL DEVICE FOR CORRECTION OF SPINAL DEFORMITIES and which was filed Dec. 10, 2008; foreign Patent Application No. GB0902416.7, which is entitled SURGICAL DEVICE FOR CORRECTION OF SPINAL DEFORMITIES and which was filed Feb. 16, 2009; foreign Patent Application No. GB0913457.8, which is entitled SURGICAL DEVICE FOR CORRECTION OF SPINAL DEFORMITIES and which was filed Aug. 3, 2009, all of which are incorporated in full by reference herein.

FIELD OF THE INVENTION

The present invention relates generally to a surgical device for the correction of deformities of the spinal column and finds particular, although not exclusive, utility in devices which are surgically implantable.

BACKGROUND OF THE INVENTION

At present, the surgical correction of deformities of the spinal column involves a surgical procedure for the insertion of fixation implant devices, such as pedicle screws or hooks, to each vertebra followed by application of external forces to achieve the desired correction of the shape of the spinal column and attachment of the said fixation devices to rigid rod-like elements to achieve permanent stabilisation of the involved part of the spinal column. Bone graft is also added to achieve permanent fusion of the same part of the spinal column.

Previous devices for correcting spinal deformities have involved the fixation of bone screws which connect to rods via pivoting connections, for example as described in WO-A2-2007/014119. Also, the use of ratchet mechanisms with spinal implants is known from WO-A2-2008/057861, WO 2007/143709 and EP-A2-1051947. Although these arrangements increase the versatility and ease of application of implants used for spinal fixation, the application of all currently used implants and methods for surgical correction of deformities of the spinal column results in the amount of correction of the deformity achieved during the surgical procedure often being limited. Furthermore, during application of all current implants and methods for surgical correction of deformities of the spinal column the entire correction is achieved during the surgical procedure and no further degree of correction is possible thereafter as the involved part of the spinal column is permanently fused. The consequences of this are the permanent loss of spinal motion and subsequent increase of the mechanical loads to the adjacent mobile spinal segments frequently leading to wear of these segments.

One device, described in US-A1-2005/0261770, has various arrangements of interconnecting vertebral supports including pivoting and sliding arrangements between the components in an attempt to avoid fusion and permanent loss of the mobility of the spinal column. However, such implants cannot be used as spinal deformity correcting devices as no means for adjusting the relative position of the vertebrae is provided. Other devices are described in US-A1-2006/155279, EP-A1-0667127, US-A1-2003/191470, U.S. Pat. No. 5,951,555, U.S. Pat. No. 5,672,175 and GB2412320 which include springs, flexible rods or other force-generating means, such as memory alloys, attempt to prevent development of the deformity or even to gradually correct a deformity of the spinal column. Although such disclosed devices are able to facilitate the development of corrective forces between parts of the spinal column most are passive and are unable to provide for the progressive correction of spinal deformities assisted by active movements of the human body. The present invention addresses this issue.

BRIEF SUMMARY OF THE INVENTION

In a first aspect, the invention provides a surgical device for the correction of deformities of the spinal column comprising a spinal column straightening means for permitting the relative rotation of two substantially adjacent vertebrae about a common axis substantially only in opposite rotational directions. The surgical device may be arranged such that, in use, the anterior edges of the end plates of two substantially adjacent vertebrae are substantially only permitted to move either closer to one another or further apart from one another. Correspondingly, the posterior edges of the end plates of two substantially adjacent vertebrae may be substantially only permitted to move either further apart from one another or closer to one another. The spinal column straightening means, in one embodiment, is a spinal column straightener.

The term "substantially" is used here in the phrase "substantially only permitted to move either closer to one another or further apart from one another" because it is contemplated that there may be an element of "play" in the device such that a slight degree of opposite relative movement occurs.

This device, which may be affixed to the posterior surfaces of vertebrae, therefore allows one of two modes of operation. The first is where adjacent vertebrae are permitted to increase their separation towards their front surfaces and/or reduce their separation towards their rear surfaces, thus straightening spines which are curved forwardly. The second is where adjacent vertebrae are permitted to decrease their separation towards their front surfaces and/or increase their separation towards their rear surfaces, thus straightening spines which are curved rearwardly. Furthermore, because the device substantially prevents rotation of the vertebrae in the opposite direction (of whichever mode of operation is selected) the device prevents the curved nature of the spine from worsening or returning to its former bent form after straightening. Moreover, as the individual stretches upwardly, thus temporarily straightening the spine, the device allows the adjacent vertebrae to straighten relative to one another but will prevent them from returning to the their previously curved form. Over time, an individual's curved spine may be corrected to one which more closely resembles a typical "straight" spine.

The term "substantially" is used with the phrase "only in opposite rotational directions" because it is contemplated that there may be an element of "play" in the device such that the adjacent vertebrae may rotate in the same direction. However, the amount of this common rotational movement may be minor compared to the opposite rotational movement effected due to the individual's typical daily activities.

The surgical device may include rotation means for permitting the relative rotation of the two said substantially adjacent vertebrae. This relative rotation may be about the common axis. In this regard, the common axis may be located within the spinal column. The rotation means may include a ratchet means. This ratchet means may be for permitting relative rotation of two substantially adjacent vertebrae about the common axis substantially only in opposite rotational directions. The ratchet may comprise well known features such as a pawl and teeth. In at least one embodiment, the rotation means is a rotation controller.

The common axis, in use, may be substantially perpendicular to the length of the spinal column. This axis may lie substantially parallel to the intersection of the coronal and transverse planes.

The surgical device may include connection means for connecting with two bone fixing elements, each element fixable, in use, to each said adjacent vertebra. In one embodiment, the connection means is connection apparatus.

The bone fixing elements may comprise substantially parallel longitudinal axes, such that, in use, the longitudinal axes are substantially parallel to the intersection of the median and transverse planes.

The common axis may, in use, be substantially perpendicular to the said longitudinal axes or intersection of the median and transverse planes.

The surgical device may further comprise rotation means for permitting, in use, the relative rotation of the two said adjacent vertebrae about an axis substantially parallel to the longitudinal axes of the bone fixing element, or intersection of the median and transverse planes.

The connection means may comprise a first male member and a first female member.

One of the two said bone fixing elements may comprise a second female member and the first male member may be connectable with this second female member.

The first male member may be rotatably and/or slidably connectable with the second female member.

The first female member may be connectable with a bone fixing element in an adjacent vertebra.

The first female member may be rotatably and/or slidably connectable with the bone fixing element.

Either or both of the first and second female members may include pivoting means for either permitting or restricting relative angular movement of any connected first male member or bone fixing element. In one embodiment, the pivoting means is a pivot controller.

The surgical device may include one or more bone fixing elements.

The surgical device may include at least one bone fixing element fixable, in use, to a first vertebra.

The surgical device may include alternative connection means for connecting with another bone fixing element fixable, in use, to a second adjacent vertebra.

The alternative connection means may comprise a first alternative female member and a first alternative male member.

The first alternative female member may be connectable with the first alternative male member of an adjacent device.

The first alternative female member may be rotatably and/or slidably connectable with the first alternative male member of the adjacent device.

The first alternative female member may include pivoting means for either permitting or restricting relative angular movement of any connected alternative male member or bone fixing element.

The first alternative female member and first alternative male member may be on opposite sides of the ratchet means.

The surgical device may include means for connecting either directly or indirectly with an adjacent similar device. When connectable directly one of the male members may be insertable into one of the female members. When connectable indirectly another intermediate element may be interposed therebetween. This intermediate element may comprise one or more male members and one or more female members, although other means of interconnection are contemplated. The intermediate element may be a rod.

In a second aspect, the invention provides a surgical device for correction of deformities of the spinal column comprising at least two mutually interconnectable segments arranged for affixation on at least two separate vertebrae of the spinal column, each segment comprising a first part, equipped with at least one bone fixing element adapted for affixation on at least one vertebra of the spinal column, a second part, connectable to the said first part at an axially arranged connection permitting rotation of the said first and second parts relative to each other around a first axis, the said second part also being equipped with at least one stem able to withstand mechanical loads during use, the said second part also being equipped with at least one connecting hole of design appropriate, firstly, to allow insertion of the said stem of at least one other segment of the surgical device disclosed herein to the said connecting hole and, secondly, to allow pivoting (angular movement) and axial sliding of the said stem in the said connecting hole, a ratchet arrangement of the said axially arranged connection between the said first and second parts permitting, in use, the said first and second parts to rotate relative to each other around the said first axis of rotation in a single predetermined direction but preventing the said first and second parts from rotating around the said first axis of rotation in an opposite direction, wherein, during use, at least two mutually interconnected segments of the surgical device disclosed herein are affixed on at least two separate vertebrae of the spinal column, the said stem of the said second part of the segment affixed on the vertebra above being axially inserted in the said connecting hole of the said second part of the segment affixed on the vertebra below, permitting angular movements between the said two vertebrae of the spinal column in the desired direction of correction of the deformity but preventing any angular movement between the said two vertebrae of the spinal column in the opposite to the said desired direction, and wherein, during normal daily activity or special exercise-induced movements of the human spinal column, any loads applied to the spinal column directed in a direction opposite to the said desired direction of correction of the said spinal deformity are endured, resisted and prevented by at least two mutually interconnected segments of the surgical device disclosed herein, whilst all other loads are endured solely by the spinal column protecting thus the surgical device disclosed herein from mechanical failure or loosening of its secure affixation on a vertebrae of the spinal column, and whereby, over a period of time, gradual correction of the said spinal deformity can be achieved without additional force generating means.

As described herein there is provided a surgical device for gradual correction of deformities of the spinal column without fusion of the involved part of the spinal column. The device may comprise mutually interconnected segments affixable to separate vertebrae of the spinal column. Their arrangement may comprise a ratchet as part of a pivoting connection between the part affixed to the bone and a support. The support may have a connecting opening to permit free relative rotation and axial movement, but which may restrict relative angulatory movement at least in one plane, between the mutually interconnected segments.

The configuration of the surgical device may permit gradual angular correction of the relative position of the vertebrae while at the same time all other movements, including those affected by axial loading of the spinal column are allowed. It is to be appreciated that gradual correction of a deformity of the spinal column may be achieved over a period of time following the application of the surgical device effected by active and passive movements of the spinal column during normal daily activities and exercising while, at the same time, the mobility of all parts of the spinal column may be preserved.

The bone fixing elements described and/or claimed herein may be of the pedicle screw variety.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DETAILED DESCRIPTION OF THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. "Connected" may mean that two or more elements are either in direct physical or that two or more elements are not in direct contact with each other but yet still co-operate or interact with each other.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may refer to different embodiments.

Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

Figure 1:
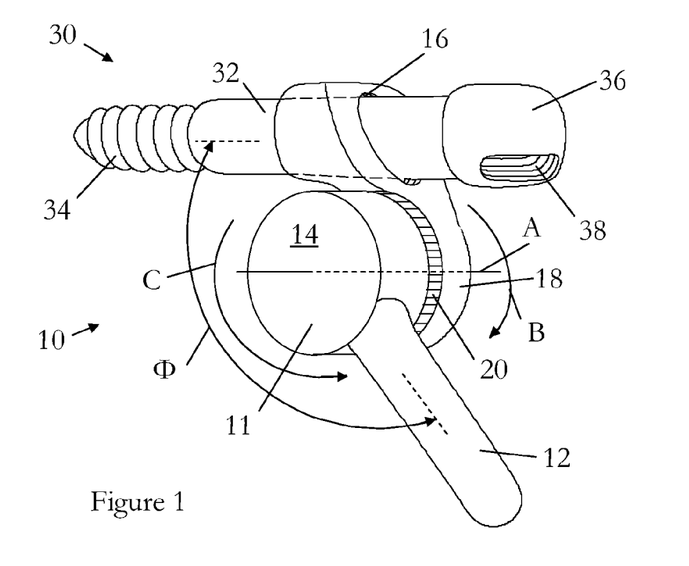
FIG. 1 is a perspective view of a device according to a first embodiment of the invention.

In FIG. 1 a surgical device 10 for the correction of deformities of the spinal column includes a rotation means 11 (substantially cylindrical in shape) for allowing rotation between two elements; the two elements being a stem, or male member, 12 and a means 18 of connecting with a bone-fixing element 30. The stem 12 is substantially cylindrical. In this embodiment, the means 18 of connecting with the bone fixing element 30 is a socket, or female member, 16 arranged on an arm radiating away from the means 11 for allowing rotation.

The rotation means 11 includes a ratchet mechanism 20 which permits the two sides of the rotation means 11 to only rotate in opposite directions relative to one another about a common axis referenced "A". In FIG. 1, the arrow referenced "B" indicates the direction in which the bone fixing element 30 is permitted to rotate, and the arrow referenced "C" indicates the direction in which the stem 12 is permitted to rotate. The angle between the longitudinal axis of the stem 12 and the longitudinal axis of the bone fixing element 30 is indicated "Φ". In use, the bone fixing element 30 and the stem 12 may only rotate in opposite directions such that the angle Φ may increase but not decrease. This restriction is effected by the ratchet 20.

The bone fixing element 30 comprises a shaft 32 having a screw thread 34 at one end and a head 36 at the other end. The head 36 is larger than the shaft 32 and of the socket 16 thus preventing the rotation means 11 from slipping off the bone fixing element 30.

The shaft 32 of the bone fixing element 30 may rotate within the socket 16 thus allowing, in use, sideways flexing (in the coronal plane) of the spinal column. The bone fixing element 30 includes a socket, or female member, in the head 38. This will be explained in more detail below.

Figure 2:
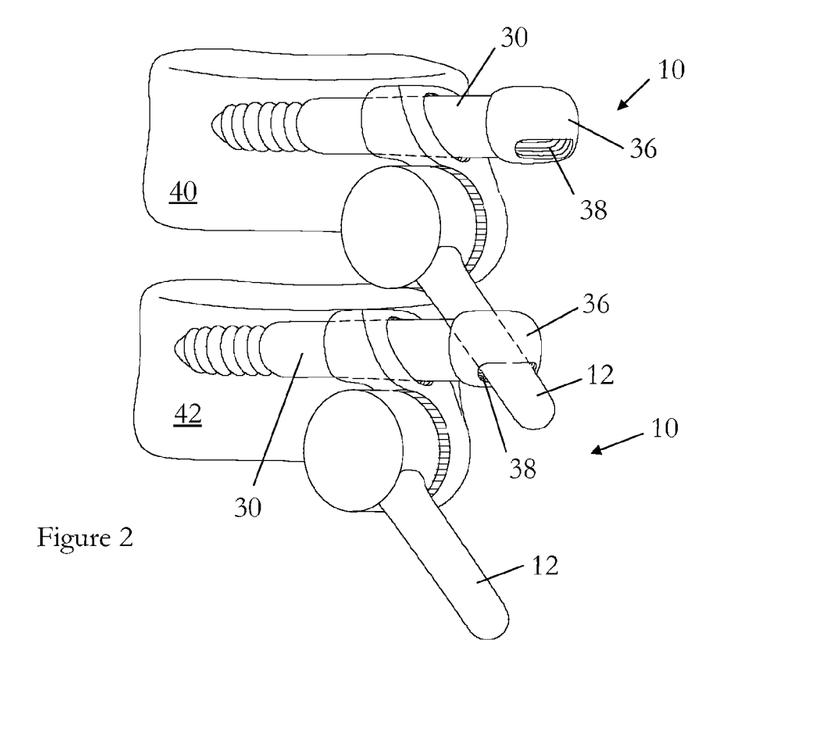
FIG. 2 is a perspective view of two of the devices of FIG. 1 in use with vertebrae.

FIG. 2 shows two devices 10 in use together with two adjacent vertebrae 40, 42. The bone fixing elements 30 have been screwed into each vertebra 40, 42 such that each device 10 is held captive thereto by the heads 36 of the respective bone fixing elements 30. The stem 12 of the upper device 10 has been inserted into the socket 38 of the bone fixing element 30 holding the lower device 10 captive. The stem 12 may rotate and move axially within the socket 38 thus allowing a certain amount of freedom of movement between adjacent vertebrae other than that restricted by the ratchet 20.

The socket 38 in head 36 of the upper bone fixing element 30 may receive a stem 12 of another device 10 (not shown) attached to a vertebra above (not shown). Likewise, the stem 12 of the lowermost device 10 may be received in the socket 38 of another device 10 (not shown) attached to a vertebra below (not shown).

Because of the ability for the various elements (bone fixing shaft 32 and socket 16; stem 12 and socket 38) to move relative to one another in one or more directions and/or planes as necessary, due to an arranged tolerance in the respective male and female members, the actual vertebrae 40, 42 do not rotate about the axis A (in FIG. 1).

Rather, they will rotate about the natural axes of the vertebrae, which will lie substantially in the sagittal, transverse and coronal planes.

Figure 3:
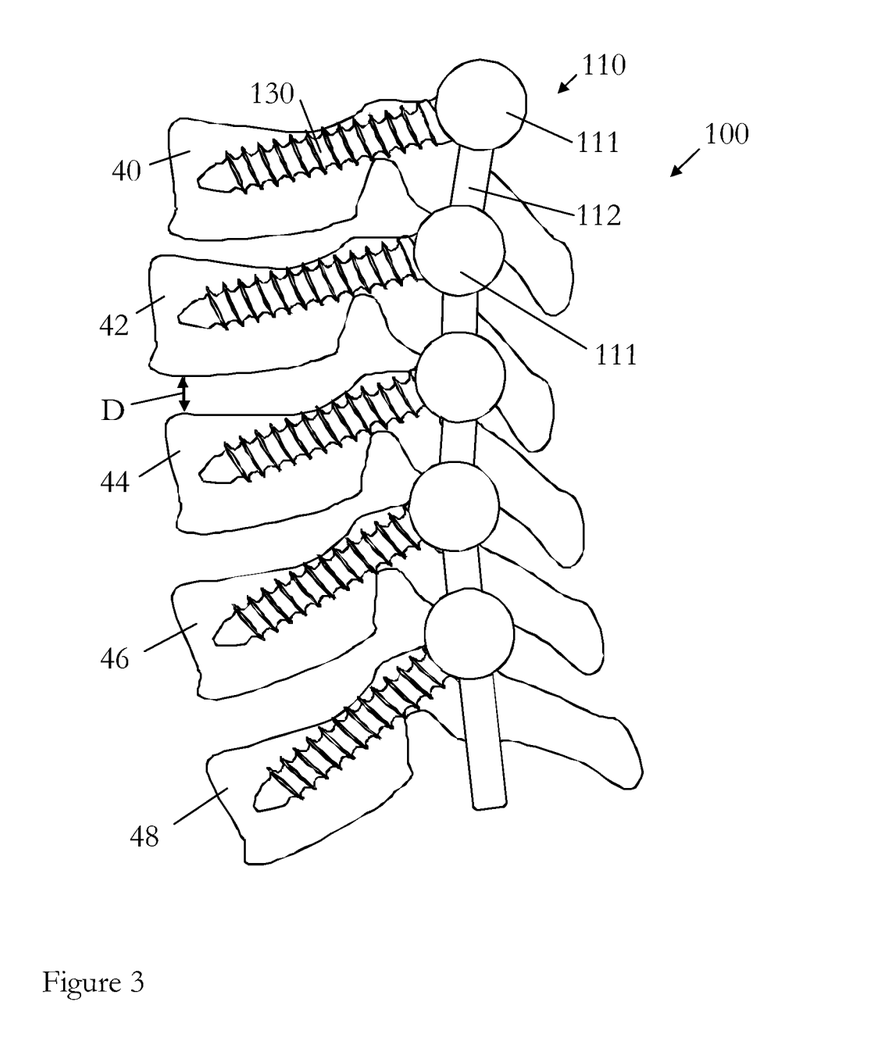
FIG. 3 is a cross-sectional side view of a series of devices according to a second embodiment of the invention in use with a series of adjacent vertebrae.

A series 100 of devices 110 may be affixed to a series of vertebrae 40, 42, 44, 46, 48 forming a portion of a spinal column as shown in FIG. 3. These devices 110 are slightly different to the devices 10 described above but operate in a similar manner. They each include a rotation means 111 (substantially cylindrical in shape) for allowing rotation between a bone fixing element 130 and a stem 112. Each stem 112 is inserted into the device 110 below.

In this way the angle Φ may be increased but not substantially decreased. This means that the vertical gap "D" between the front edges of adjacent vertebrae may be increased but not substantially decreased.

Figure 4:
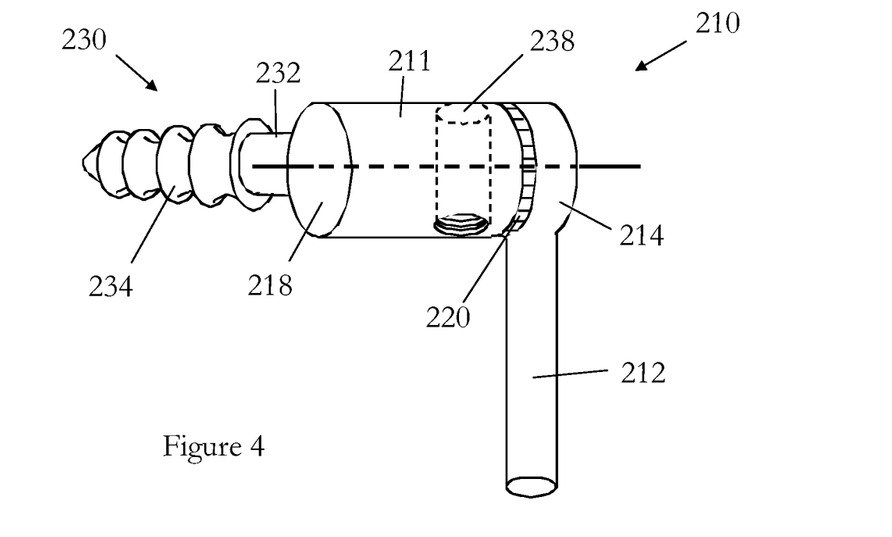
FIG. 4 is a perspective view of a device according to a third embodiment of the invention.

A third embodiment of the device 210 is shown in FIG. 4. It comprises a stem 212 attached to one side 214 of a rotational ratchet 220, and a bone fixing element 230 comprising a screw thread 234 and a shaft 232 directly attached to the other side 218 of the ratchet 220. The two sides 214, 218 make up the rotation means 211 (which is substantially cylindrical in shape). The ratchet 220 restricts relative rotational movement of the two sides in a similar manner to that described above.

In this embodiment, a socket 238 is provided in the body of the rotation means 211. This socket may receive a stem 212 from an adjacent device 210, in a similar manner to that described above, such that an array of devices 210 may be interconnected. The socket 238 is arranged such that the stem 212 may rotate and move axially and angularly within it thus allowing a certain amount of freedom of movement between adjacent vertebrae other than that restricted by the ratchet 20.

Figure 5:
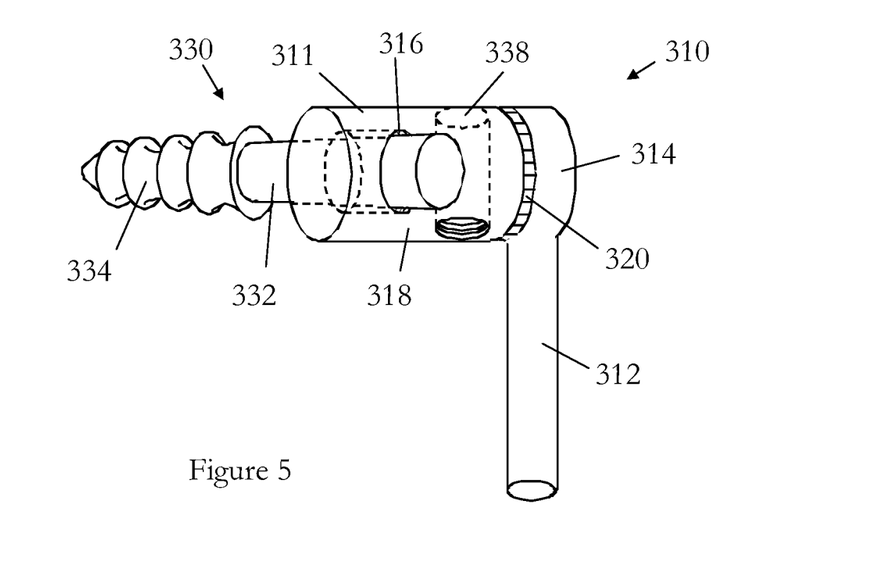
FIG. 5 is a perspective view of a device according to a fourth embodiment of the invention.

A fourth embodiment of the device 310 is shown in FIG. 5. This device 310 is similar to the device 210 shown in FIG. 4 except that the shaft 332 of the bone fixing element 330 is not directly attached to the rotation means 311, which is substantially cylindrical in shape. Rather, a socket 316 is provided in the body of the rotation means 311 adjacent the socket 338 for receiving the stem 312 of an adjacent device 310. This socket 316 may receive the shaft 332 of the bone fixing element 330. The socket 316 is arranged such that the stem 312 may rotate and move axially and angularly within it thus mallowing a certain amount of freedom of movement between adjacent vertebrae other than that restricted by the ratchet 20. This is more clearly shown in FIG. 6.

Figure 6:
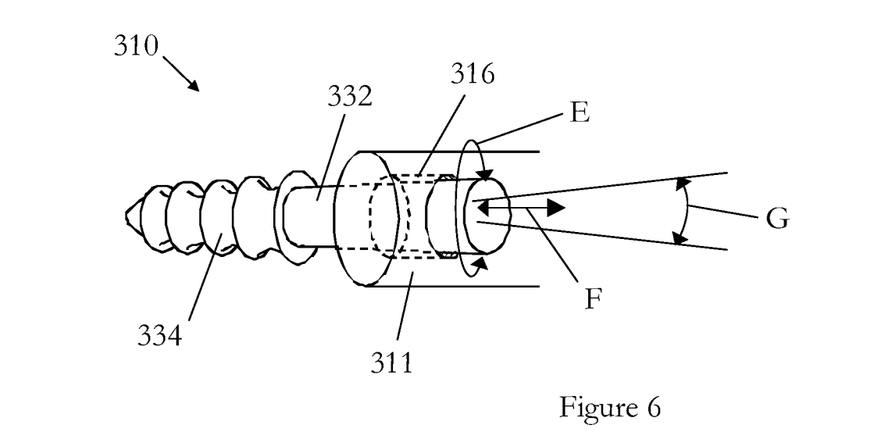
FIG. 6 is a close-up perspective view of the device of FIG. 5.

The axial movement is referenced "F", the rotational movement is referenced "E", and the angular movement is referenced "G". All other features are the same as described with regard to FIG. 5.

Figures 7, 8:
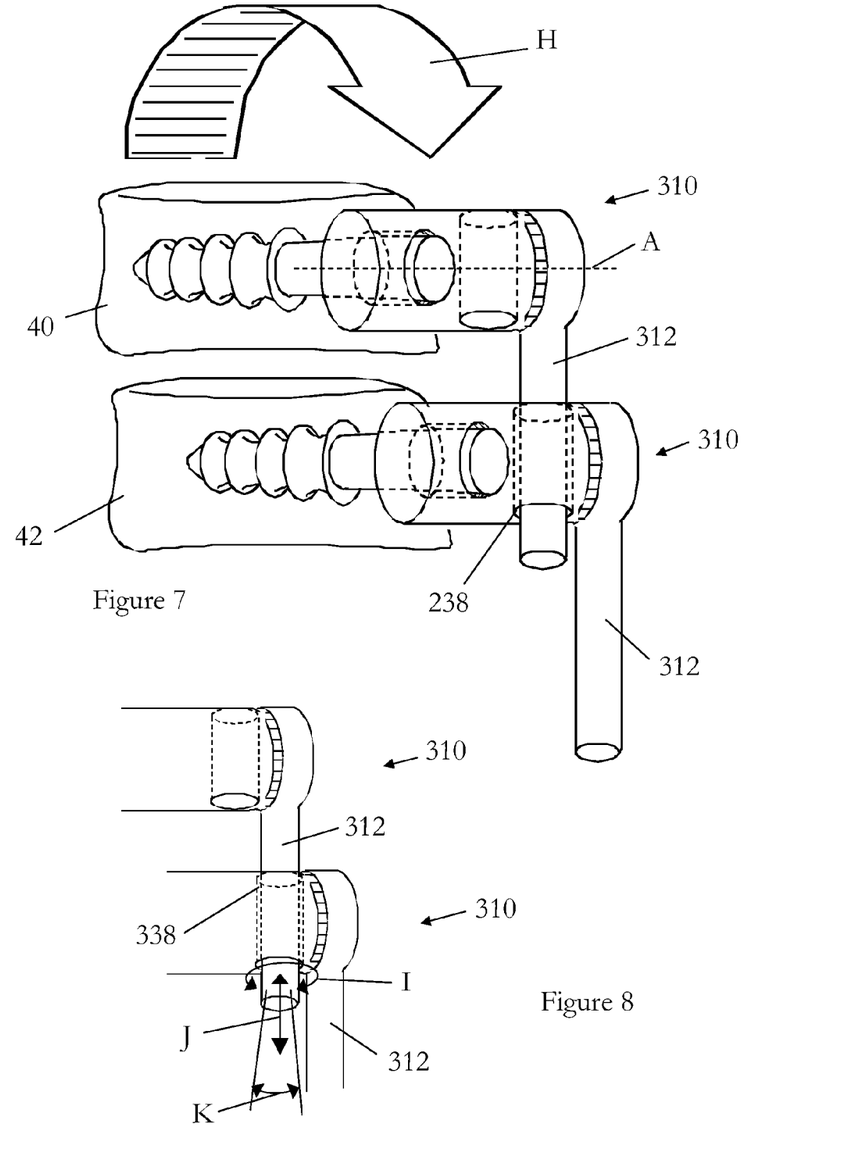
FIG. 7 is a perspective view of two of the devices of FIG. 5 in use with two vertebrae.
FIG. 8 is a close-up perspective view of the two devices of FIG. 7.

FIG. 7 shows two devices 310 arranged together, and connected or affixed to two adjacent vertebrae 40, 42, such that the stem 312 of the upper device 310 is inserted into the socket 238 of the lower device 310. The arrow referenced "H" indicates the direction in which the upper vertebrae 40 may rotate relative to the axis of rotation "A". FIG. 8 indicates the rotational "I", axial "J" and angular "K" movement which the upper stem 312 may make relative to the lower socket 338. There may also be some rotational movement therebetween (not shown).

Figure 9:
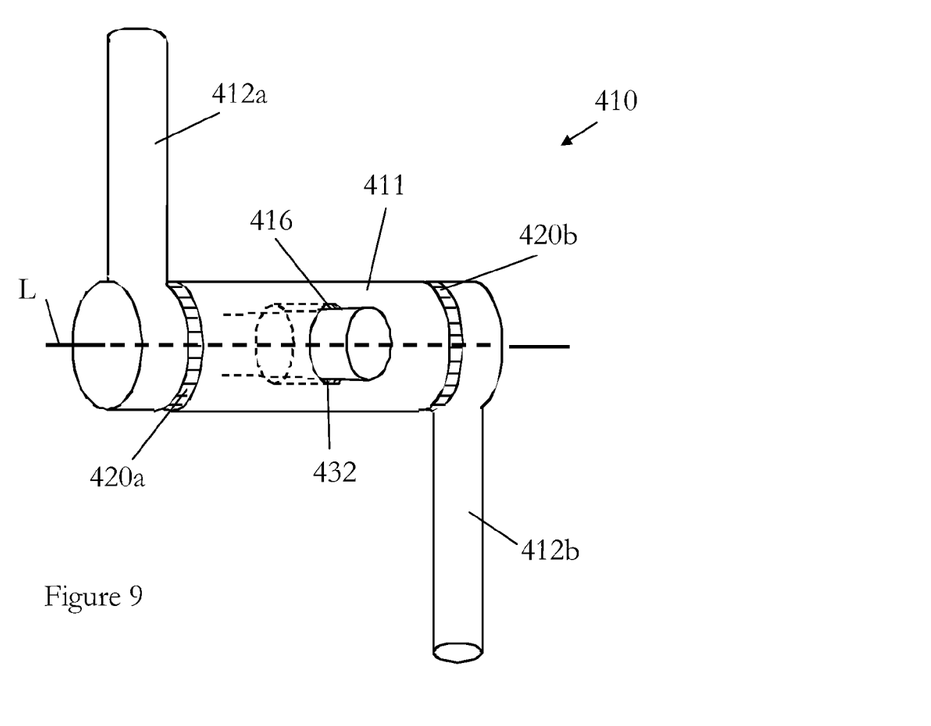
FIG. 9 is a perspective view of a device according to a fifth embodiment of the invention.
Figure 10:
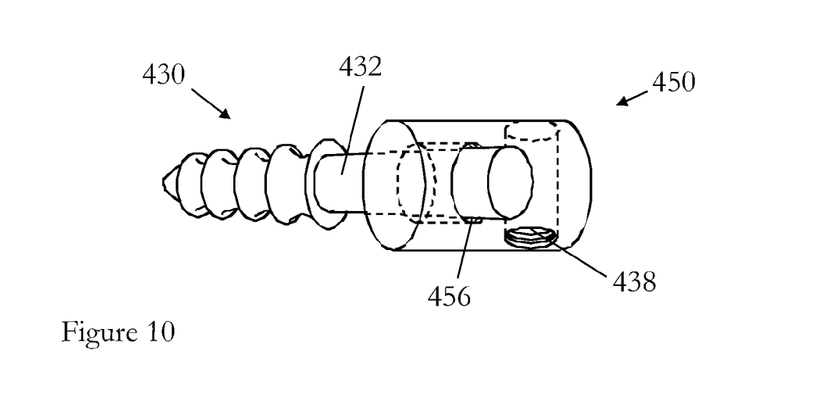
FIG. 10 is a perspective view of a device according to a sixth embodiment of the invention.

A different embodiment of the device 410 is shown in FIG. 9. This device 410 has a rotation means 411 (substantially cylindrical in shape) comprising two ratchets 420a, 420b separating the rotation means 411 into three portions. At each end portion of the rotation means 411 a stem 412a, 412b is provided projecting radially away. A socket, or female member, 416 is provided radially through the middle portion of the rotation means 411. This socket 416 may receive a shaft 432 of a bone fixing element 430 (refer to FIG. 10) such that it may be affixed to vertebra. Each stem 412a, 412b may connected to a bone fixing element 43 either directly or indirectly. An example is shown in FIG. 10. The device 450 comprises a substantially cylindrical element comprising two sockets, or female members, 438, 456 which pass radially through the cylindrical element from one side to the other. These two sockets 438, 456 are aligned such that their respective bores are substantially perpendicular to one another. The shaft 432 of a bone fixing element is shown inserted into one of the sockets 456. The other socket 438 may receive one of the stems 412a, 412b described above. Two devices 450 may be arranged one on each stem 412a, 412b. By virtue of ratchet 420a the upper bone fixing element, in device 450, and the one in the rotation means 411 may rotate relative to one another but only in opposite directions. Also, by virtue of ratchet 420b the lower bone fixing element, in another device 450, and the one in the rotation means 411 may rotate relative to one another but only in opposite directions.

The relative rotation of the two sets of bone fixing elements 430 may rotate around a common axis referenced "L" passing through the longitudinal central axis of the substantially cylindrical rotation means 411.

Figure 11:
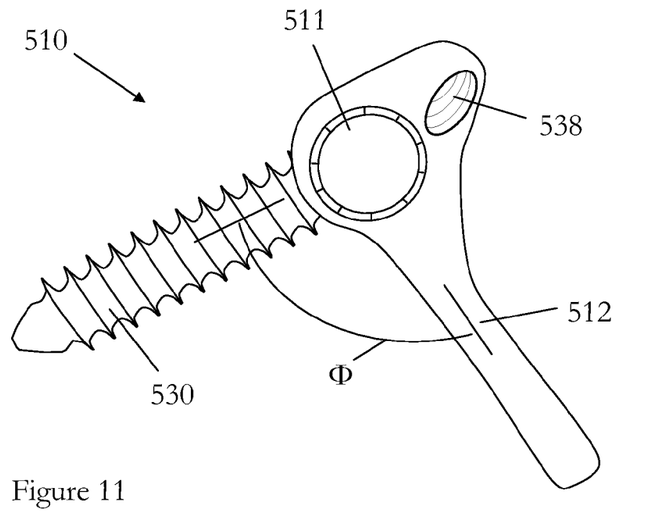
FIG. 11 is a perspective view of a device according to a seventh embodiment of the invention.

FIG. 11 shows yet another embodiment of the device 510. This device 510 includes a bone fixing element 530 rotatably connected to one side of a rotation means 511. On the other side of the rotation means 511 a stem, or male member, 512 is provided. The stem 512 and bone fixing element 530 may rotate relative to one another limited by some means, possibly a ratchet means (not shown), such that they may only rotate away from each other (as shown in the Figure) so that angle Φ may be increased but not substantially decreased.

Figure 12:
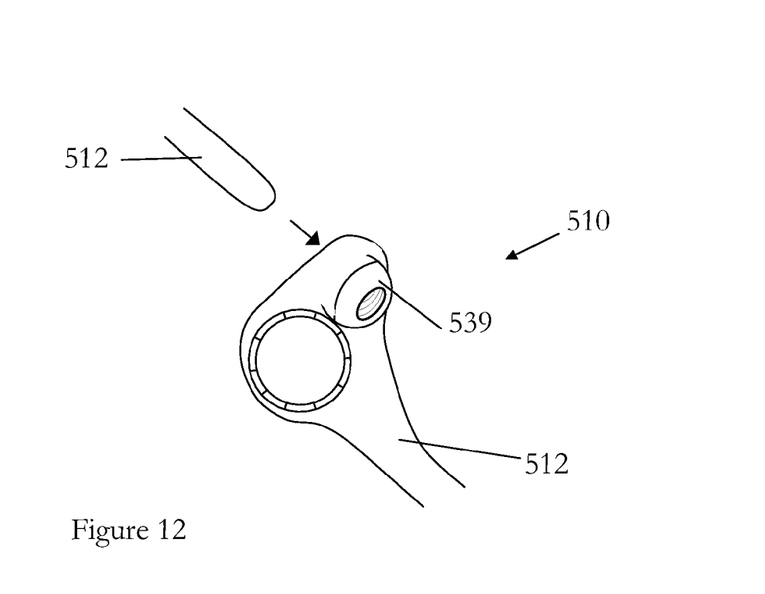
FIG. 12 is a perspective view of the device of FIG. 11 with an alternative feature.

A socket, or female member, 538 is provided with the rotation means 511 for receiving a stem 512 from an adjacent device 510 as shown in FIG. 12. The position of the socket 538 is arranged substantially on the same axis as the longitudinal length of the bone fixing element 530. However, the longitudinal axis/direction of the bore of the socket 538 is substantially perpendicular to the longitudinal axis of the bone fixing element 530.

This Figure, (bone fixing element 530 removed for clarity purposes) also includes a variant to the device 510 shown in FIG. 11 in that the socket 539 is a ball socket. This allows angular as well as axial and rotational movement of the stem 512 of the adjacent device 510 relative to the device 510.

Figure 13:
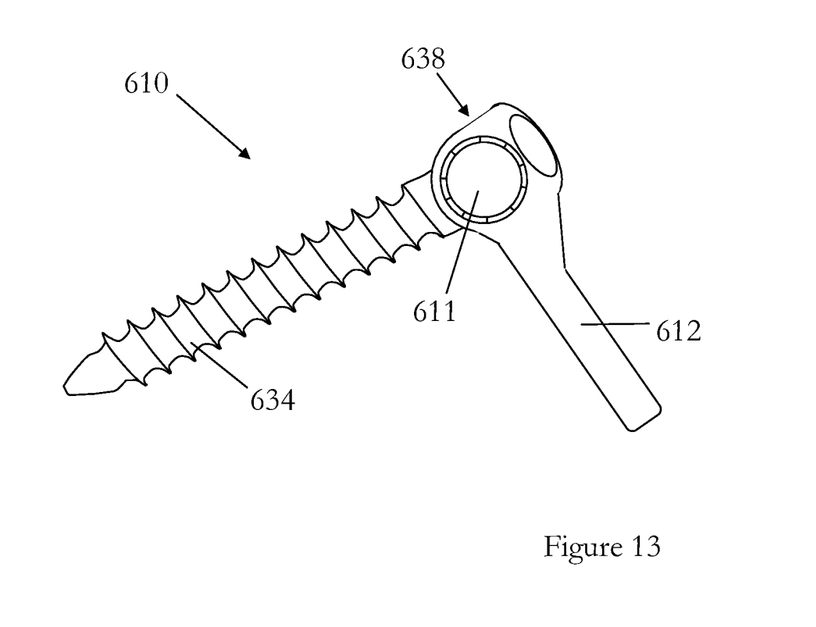
FIG. 13 is a perspective view of a device according to an eighth embodiment of the invention.
Figure 14:
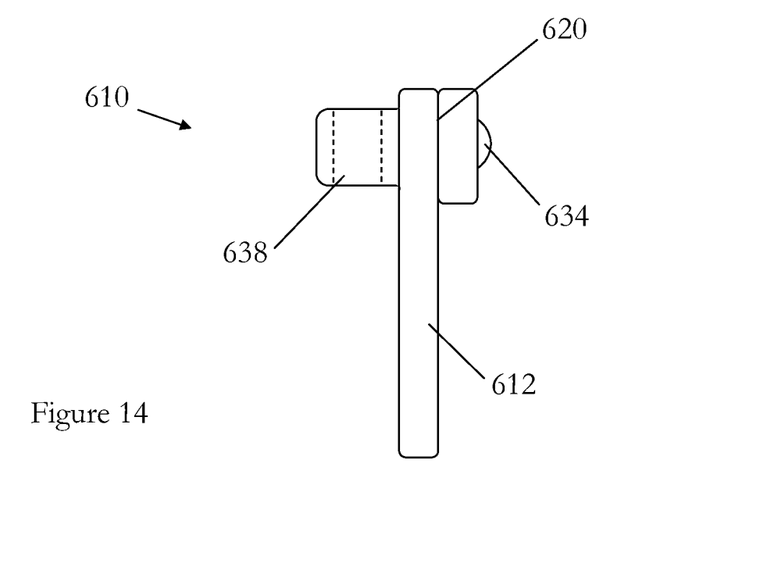
FIG. 14 is a rear elevational view of the device of FIG. 13.

Another embodiment is shown in FIGS. 13 and 14. This device 610 is similar to the device 510 described above, having a rotation means 611 and a bone fixing element 634. However, the socket 638 for receiving the stem 612 of an adjacent device 610 is arranged to one side of the bone fixing element 634 as is more clearly shown in FIG. 14. This view is from "behind" the device 610 looking along the length of the bone fixing element 634. The socket 638 is arranged on the other side of the ratchet means 620 from the bone fixing element 634 and has its bore substantially perpendicular to the longitudinal length of the bone fixing element 634.

Figure 15:
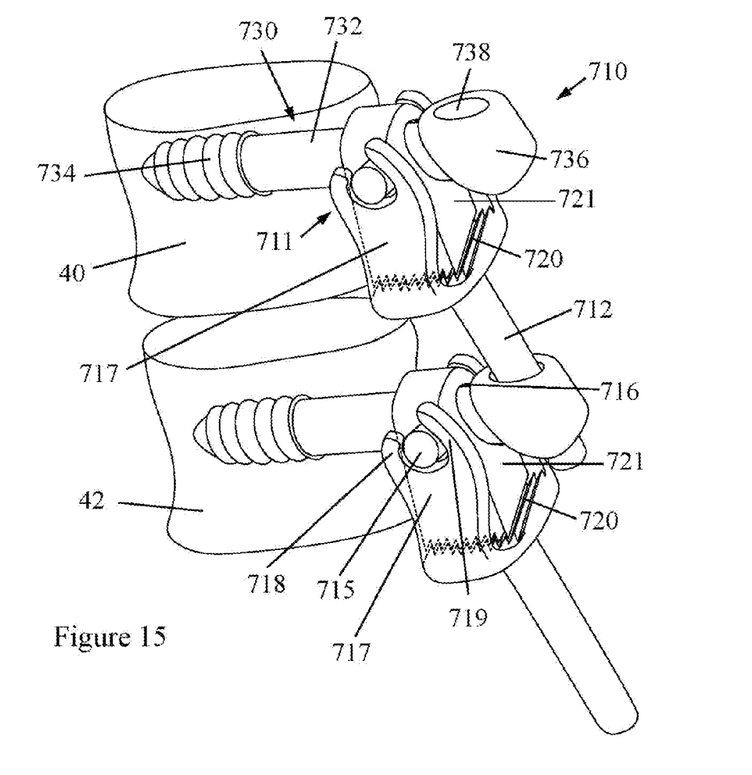
FIG. 15 is a perspective view of a device according to an ninth embodiment of the invention.

A ninth embodiment is shown in FIG. 15. This embodiment 710 comprises a bone fixing element 730 which comprises a thread 734, a shaft 732 and a head 736. The head includes a socket 738 for receiving the stem 712 of an adjacent device 710. The stem 712 is attached to, or integral with an outer part 717 of the rotation means 711. This rotation means permits relative rotation between the stem 712 and the bone fixing element 730 around an axis which substantially lies along the intersection of the transverse and coronal planes. At the base of the outer part 717 of the rotation means 711 the stem 712 is connected, and at the upper end of the outer part 717 of the rotation means 711 two arms 718, 719 are provided. On the inner part 721 of the rotation means 711 are provided two axles or pins 715 (only one being shown) around which the two arms 718, 719 are arranged thus allowing relative rotation of the inner and outer parts 717, 721.

The inner part 721 of the rotation means 711 also includes a female socket 716 through which the shaft 732 of the bone fixing element 730 is arranged allowing relative rotational movement between the bone fixing element 730 and the stem 712 about the longitudinal axis of the bone fixing element 730.

The rotation means 711 includes a ratchet 720 which in this case comprises a set of teeth on one of the inner and outer parts 717, 721 and a pawl on the other of the inner and outer parts. It is possible that the pawl is another set of teeth, the sets of teeth arranged and provided to allow them to slide over one another in one direction but prevent them sliding over one another in the other direction.

Figure 16:
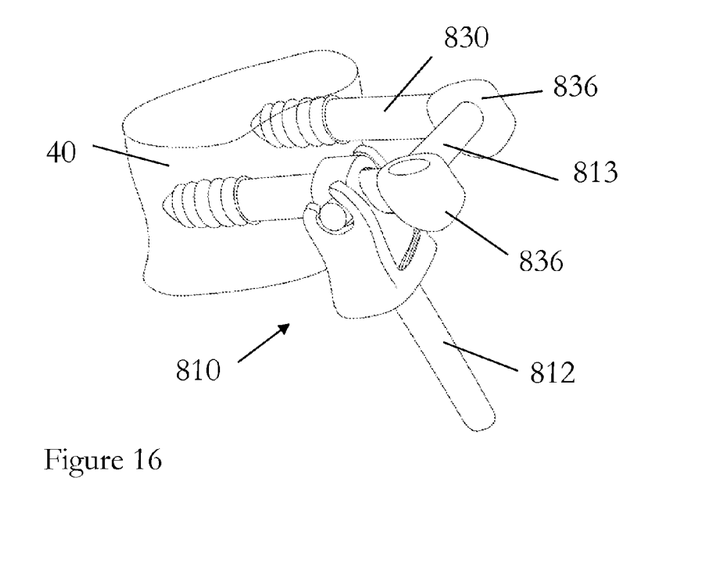
FIG. 16 a perspective view of a device according to an tenth embodiment of the invention.

FIG. 16 shows an embodiment 810 which is similar to the ninth embodiment described in conjunction with FIG. 15. The only difference is that device 810 includes a means for attaching another transverse stem 813 to the head 836 of the bone fixing element 830. Alternatively, the transverse stem may be integral with the head 836.

Another bone fixing element 830 is provided in the same vertebra 40 and arranged laterally to one side of the other. The transverse stem 813 connects the heads 836 of the two bone fixing elements 830. In this way greater stability is provided to the structure and to the spinal column. It should be understood that the concept of an additional bone fixing element 830 and interconnection between the two bone fixing elements 830 in the same vertebra may be applied to any of the other embodiments described herein.

In the foregoing description of the various embodiments, it has been explained how the angle Φ may increase but not decrease. It is to be understood that the opposite effect is also possible, namely that the angle Φ may decrease but not increase. This restriction may be effected by appropriate arrangement of the ratchet as required.

Although when describing the various sockets, or female members, 38, 238, 316, 338, 416, 456, 438, 538, 539, 638 it has been explained that they are arranged to allow relative rotational, axial and angular movement with the stem or shaft it should be understood that in some embodiments it may be desirable to limit or even restrict some or all of this allowance. It is possible to include means, such as contoured surfaces, for permitting only relative movement between the stem, and/or shaft, and socket in one or more directions (axial, rotational, angular) and/or planes (sagittal, coronal, transverse).

For instance it may be preferred to restrict relative angulatory movement in one or more planes such as the sagittal plane.

Any of the embodiments described herein may include a ball joint in any of the female sockets.

Furthermore, although not all of the bone fixing elements 30, 330, 430 are shown including a head of greater size than the socket through which they may be inserted it is to be understood that they may include such a head to prevent them from disengaging with their corresponding devices and/or rotation means.

The invention claimed is:

1. A surgical device for the correction of deformities of the spinal column comprising:
   a spinal column straightener having two bone fixing elements each attachable to a vertebra of a spinal column, and a connection apparatus for connecting the two bone fixing elements, the connection apparatus including a stem and a female socket for connecting with at least one of said bone fixing elements, and a rotation controller for permitting relative rotation of the two bone fixing elements about a common axis, wherein the rotation controller includes a ratchet such that the two bone fixing elements are permitted to rotate about a common axis parallel to the intersection of the coronal and transverse planes substantially only in opposite rotational directions so that over a period of time following the installation of the two bone fixing elements into two substantially adjacent vertebra and the connection together of the two bone fixing elements with the connection apparatus, and effected by active and passive movements of the spinal column during normal daily activities and exercising, gradual correction of a deformity of the spinal column is achievable by substantially only permitting the anterior edges of the end plates of the two substantially adjacent vertebrae to move either closer to one another, or further apart from one another.

2. The surgical device of claim 1, wherein the common axis, in use, is substantially perpendicular to the length of the spinal column.

3. The surgical device of claim 1, wherein the bone fixing elements comprise substantially parallel longitudinal axes, in use, and the common axis is, in use, substantially perpendicular to said parallel longitudinal axes.

4. The surgical device of claim 1, wherein the rotation controller is arranged to permit, in use, the relative rotation of the two said substantially adjacent vertebrae about an axis substantially parallel to the longitudinal axes of the bone fixing element.

5. The surgical device of claim 1, wherein one of the two said bone fixing elements comprises a bone fixing element socket and the stem is connectable with this bone fixing element socket.

6. The surgical device of claim 5, wherein the stem is rotatably and/or slidably connectable with the bone fixing element socket.

7. The surgical device of claim 5, wherein either or both of the female socket and bone fixing element socket include a contoured surface for either permitting or restricting relative angular movement of any connected stem or bone fixing element.

8. The surgical device of claim 1, wherein the female socket is connectable with the bone fixing element in an adjacent vertebra.

9. The surgical device of claim 8, wherein the female socket is slidably and/or rotatably connectable with the bone fixing element.

10. A method for surgically correcting deformities of the spinal column, the method comprising:
  affixing two bone fixing elements to two adjacent vertebra of a spinal column;
  connecting the two bone fixing elements with a connection apparatus, the connection apparatus including a stem and a female socket, and a rotation controller;
  wherein the rotation controller includes a ratchet such that it permits relative rotation of the two bone fixing elements about a common axis parallel to the intersection of the coronal and transverse planes substantially only in opposite rotational directions so that over a period of time following the affixing of the two bone fixing elements and effected by active and passive movements of the spinal column during normal daily activities and exercising, gradual correction of a deformity of the spinal column is achievable by substantially only permitting the anterior edges of the end plates of the two substantially adjacent vertebrae to move either closer to one another, or further apart from one another.

11. The method of claim 10, further comprising:
  providing one of the two said bone fixing elements with a bone fixing element socket;
  connecting the stem with this bone fixing element socket; and
  providing suitable contoured surfaces for either or both of the female socket and bone fixing element socket to either permit or restrict relative angular movement of any connected stem or bone fixing element.

\* \* \* \* \*